(12) United States Patent
Landtbom

(10) Patent No.: US 9,962,280 B2
(45) Date of Patent: May 8, 2018

(54) ORTHOPEDIC SUPPORT WITH MAGNETS

(71) Applicant: William Andrew Landtbom, San Francisco, CA (US)

(72) Inventor: William Andrew Landtbom, San Francisco, CA (US)

(*) Notice: Subject to any disclaimer, the term of this patent is extended or adjusted under 35 U.S.C. 154(b) by 279 days.

(21) Appl. No.: 14/705,384

(22) Filed: May 6, 2015

(65) Prior Publication Data
US 2015/0351946 A1    Dec. 10, 2015

Related U.S. Application Data

(63) Continuation-in-part of application No. 14/204,492, filed on Mar. 11, 2014.

(51) Int. Cl.
A61F 5/00    (2006.01)
A61F 5/02    (2006.01)
A61F 5/30    (2006.01)

(52) U.S. Cl.
CPC .............. *A61F 5/028* (2013.01); *A61F 5/30* (2013.01)

(58) Field of Classification Search
CPC .................................. A61F 5/028; A61F 5/30
USPC ............................................. 602/19; 128/876
See application file for complete search history.

(56) References Cited

U.S. PATENT DOCUMENTS

| | | | | |
|---|---|---|---|---|
| 5,429,587 A | * | 7/1995 | Gates | A61F 5/028 128/876 |
| 5,450,858 A | * | 9/1995 | Zablotsky | A61F 5/012 128/876 |
| 5,993,375 A | * | 11/1999 | Engel | A61N 2/008 600/15 |

* cited by examiner

*Primary Examiner* — Kristen Matter
(74) *Attorney, Agent, or Firm* — David E. Lovejoy

(57) ABSTRACT

Disclosed is an orthopedic support for securing about the lumbar region of a wearer. The support includes a smoothly contoured body having a template surface bounded by an upper margin and a lower margin. A central trough extends between the upper and lower margins for accommodating the spinal processes of a wearer when the template surface is pressed against the lumbar region. Two raised plateau regions flank the central trough for contacting the erector spinae muscles of the wearer to provide support therefor. The central trough and the plateau regions form a smoothly curving surface approximating the lordotic curve of a wearer to assist maintaining spinal posture. A magnetic pad is attached to the contoured template surface and extends between the margins and extends over the central trough between the two raised plateau regions to provide a therapeutic magnetic field to the lumbar region.

18 Claims, 14 Drawing Sheets

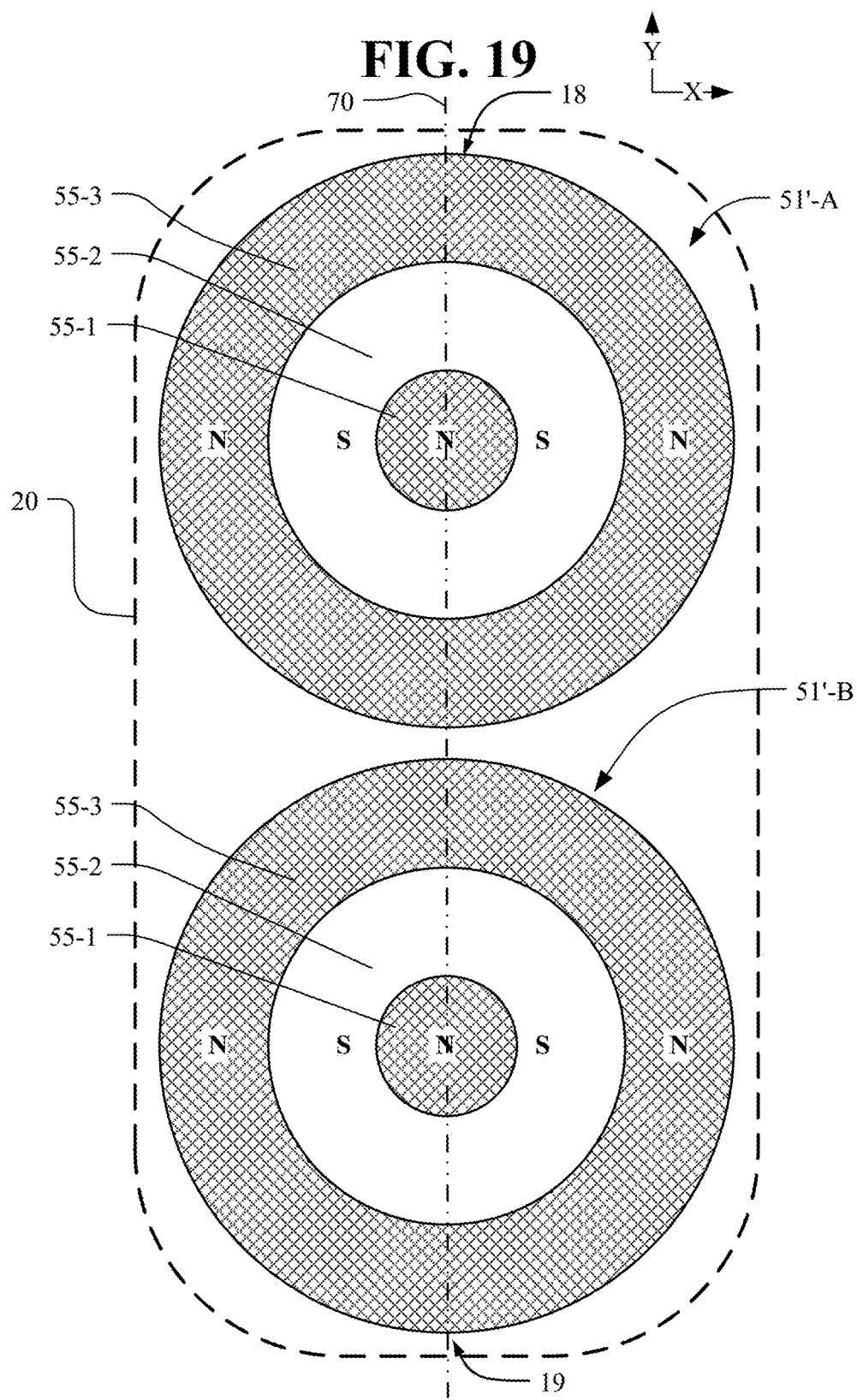

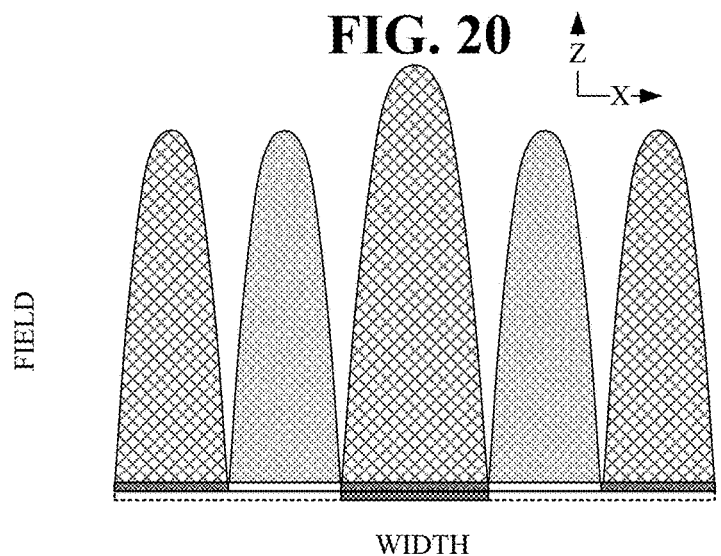
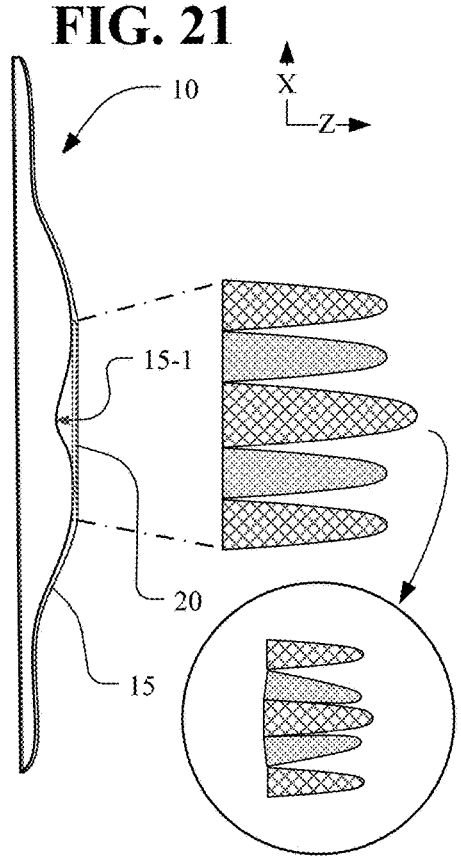
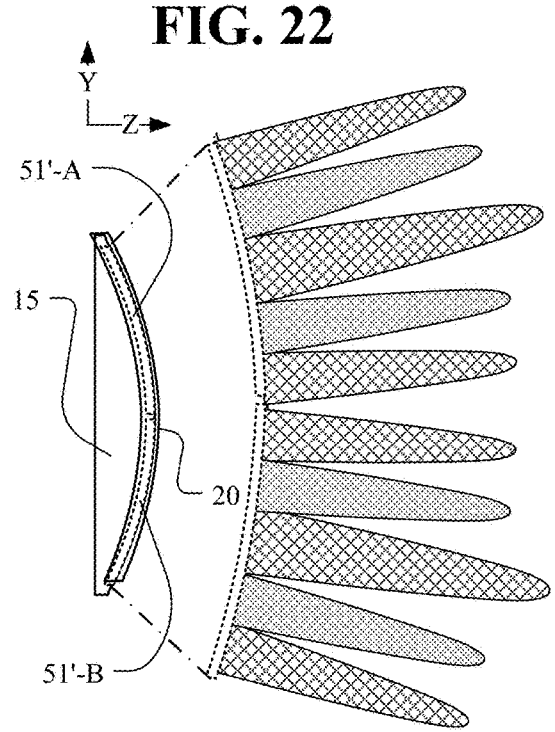

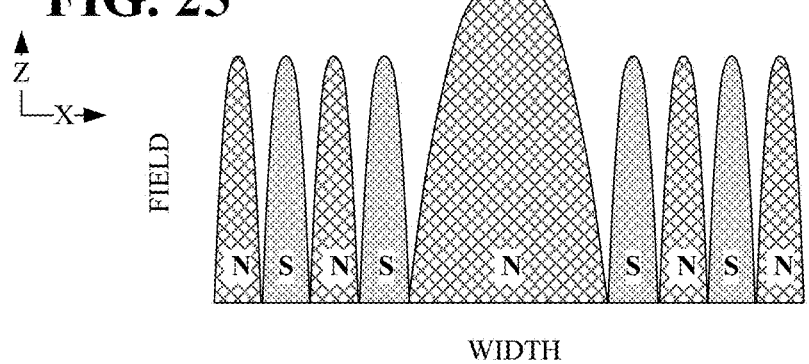
FIG. 25
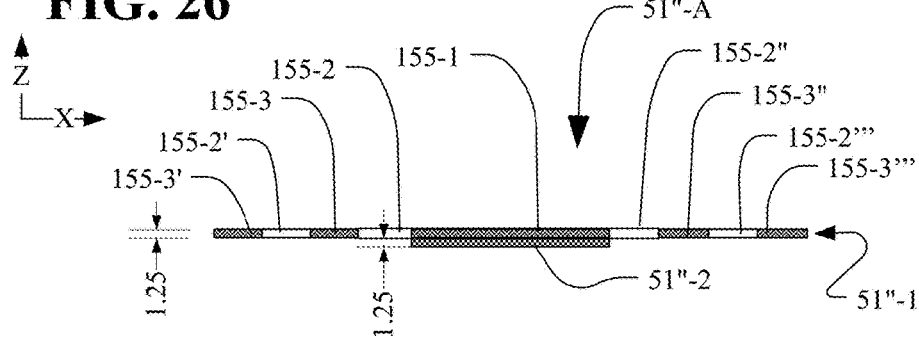
FIG. 26
FIG. 27
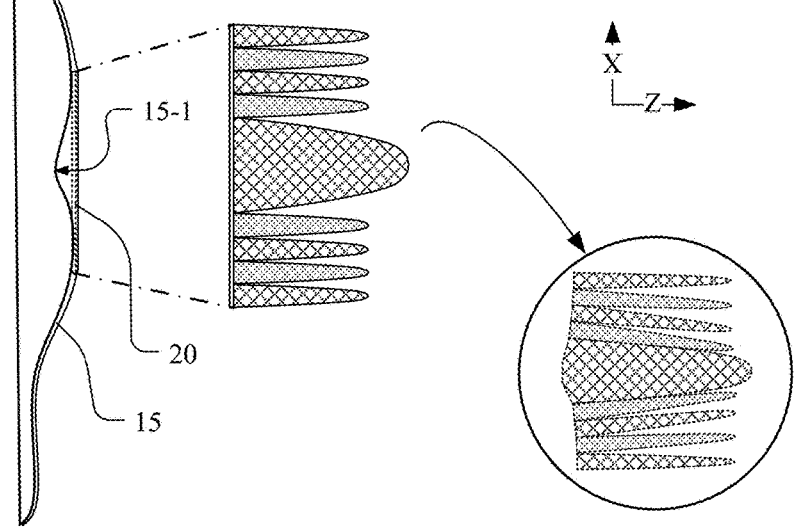

ORTHOPEDIC SUPPORT WITH MAGNETS

BACKGROUND OF THE INVENTION

This invention relates to orthopedic devices for providing support, pain relief or injury prevention for the lower back. More particularly, this invention relates to an orthopedic device including a support with magnets adapted to be worn by a user to provide support, pain relief or injury prevention for the user.

The cause of back injuries and pain can be stated: "It's not WHAT you lift, but HOW you lift, and HOW you do everything else". Only 4% of back injuries are "one-event" situations, where the cause is easily definable. The rest involve a level of repetitive motion damage, exacerbated by poor postural transitions, stretching spinal tissues, degrading them until they reach the "ready-to-go" stage. A simple sneeze or tying one's shoes can be the final straw, but these injuries are normally termed as "lifting" injuries.

Many orthopedic devices in the form of supports have been proposed to provide lower back support to avoid injuries and to prevent or alleviate lower back pain. Supports designed for this purpose have generally been of two different types. A first type uses a conforming pad, typically made of foam material, with the pad being permanently attached to the support, either inside or outside the fabric of the support, with the pad in a position to be compressed against the lower back region when the support is arranged about the waist of the user. The second type employs an inflatable air bladder having one or more air chambers with the wall of the bladder being sufficiently flexible to enable the air chamber to conform to the shape of the back of the wearer when the support is attached around the waist.

Both types of support devices suffer from the disadvantage that the portion of the device in contact with the back of the user (the pad or the air chamber walls) functions to easily conform to the shape of the wearer's back. Consequently, if the lower back is in a position other than for ideal posture, the support does not promote a change to the proper posture since the contact region of the pad adapts to the shape of the lower back. When this shape is contorted, as for example by performing a stressful lifting routine, the back is not effectively impeded by the device from maneuvering to an improper posture.

There have been many variations of back supports over the years. For example, elastic back supports have been available with and without suspenders. The supports are wrapped tightly around the waist and cinched with Velcro or similar closures. These devices made several safety claims, such as "This product will conform to the wearer's body, for comfort" or "This product should be tightened during any lifting activities, but loosened and allowed to hang untightened by the suspenders during non-lifting periods". If metal stays were present, the claim was often made that "The metal stays will remind the wearer to lift properly". While many support devices have been and are available, they do not properly or adequately provide support and improvement of spinal mechanics or relieve or prevent pain. These devices conform to the body and do not provide a template to which the spine will conform.

A dramatic improvement in orthopedic supports has been provided in the devices described in U.S. Pat. No. 5,429,587 entitled ORTHOPEDIC PAD and U.S. Pat. No. 5,651,763 entitled ORTHOPEDIC BELT. These patents describe orthopedic devices that provide a lumbosacral support system comprising a support and an orthopedic pad carried by the support. The orthopedic pad has a contoured template surface with a transversely extending central trough portion for accommodating the protruding spinal processes of the wearer when the pad is pressed against the lumbar region, and a pair of raised plateau regions flanking the central trough portion for contacting the erector spinae muscles of the wearer to provide support and improvement of spinal mechanics. The template surface of the pad has a vertical surface contour through the central region approximating the average lordotic curve of a wearer. The support is longitudinally tapered so the pad is arranged at an angle to vertical to optimally engage the lumbar region of the wearer.

The devices described in U.S. Pat. Nos. 5,429,587 and 5,651,763 provide a firm, curved surface, pressed against the spine that tends to assist spinal tissues to maintain correct spinal posture by conforming to the surface of the curved, firm lumbar pad. Later, a Harvard Med School paper found that a "curved, firm surface" created "proprioceptive feedback", a subconscious effect where the spine would conform to a predetermined lumbar pad, improving spinal mechanics. This dynamic occurs where spinal tissues act independently of the conscious mind, to reorient their positioning in order to stay within a safe range of motion. Because poor spinal mechanics becomes an ingrained habit, change is very difficult to achieve at the conscious level. Additionally, two peer reviewed studies found that this lumbar pad did maintain a safe range of motion in a simple reaching task (no lifting, where the conscious mind would take over) and credited the result to "proprioceptive feedback". Finally, the American Osteopathic Academy of Sports Medicine, in granting Back-A-Line, the owner of U.S. Pat. Nos. 5,429,587 and 5,651,763, the only Seal of Acceptance granted in their history, also praised the curved, firm lumbar pad as the reason.

Magnets have also been proposed for relieving pain in the lower back region. Magnetic therapy is intended to relieve pain, improve circulation and promote healing. Magnetic therapy to be effective requires magnets that adequately deliver an effective magnetic field of sufficient depth over the entire lumbar region. There are many different types of magnets and many of them have no significant therapeutic effect.

Spinal weakening or damage occurring because of poor spinal mechanics often result in chronic back pain due to swollen or stretched tissues and insufficient blood flow. Even if back pain is treated with magnetic therapy, however, such treatment does not improve spinal mechanics nor eliminate the risk of future spinal damage. The prior spinal mechanics may have resulted in compressed disks, stretched and weakened ligaments and other problems that would result in (cur-rent) "residual pain" and would continue to deteriorate further without the introduction of improvements to the spinal mechanics.

Existing "residual pain", caused by prior poor spinal mechanics or other problems, when treated by magnetic therapy will not improve significantly unless the magnets are of sufficient strength and characteristics to access the lumbar region and the affected spinal tissues. Such "residual pain" may also lead to undesirable compensating spinal mechanics as a means of lessening the existing pain, but such compensating spinal mechanics may cause other negative effects on the tissues that do the compensating.

In consideration of the above background, there is a need for improved orthopedic supports that improve spinal mechanics, reduce pain in the lumbar region and provide relief for chronic back pain from prior spinal damage.

SUMMARY

The present invention is an orthopedic support for securing a magnetic pad about the lumbar region of a wearer. The support includes a smoothly contoured body having a template surface bounded by an upper margin and a lower margin. A central trough extends between the upper and lower margins for accommodating the spinal processes of a wearer when the template surface is pressed against the lumbar region. Two raised plateau regions flank the central trough for contacting the erector spinae muscles of the wearer to provide support therefor. The central trough and the plateau regions form a smoothly curving surface approximating the lordotic curve of a wearer to assist maintaining spinal posture. A magnetic pad is affixed to the contoured template surface and extends between the margins and extends over the central trough between the two raised plateau regions to provide a therapeutic magnetic field to the entire lumbar region.

In one embodiment, the magnetic pad is formed of a flexible binding material that is depressed into the central trough when the template surface is pressed against the lumbar region.

In one embodiment, the magnetic pad is formed of a concentric circle magnet containing concentric circle partitions.

In one embodiment, the magnetic pad is formed of concentric circle first and second magnets where the first and second magnets are juxtaposed and where the first and second magnets are each centered on a line between the upper and lower margins.

In one embodiment, the first and second magnets each have multiple conic section alternating North (N) and South (S) polarities.

In one embodiment, the first and second magnets each have a NSNSN configuration or a SNSNS configuration.

In one embodiment, the first and second magnets each have a SNSNSNSNSNS configuration or a NSNSNSN-SNSN configuration.

In one embodiment, the concentric circle magnet contains a first layer formed of a center circle and a plurality of concentric circle partitions around the center circle and a second layer formed of a linear magnet juxtaposed the center circle where the polarity of the center circle and the linear magnet are the same.

In one embodiment, the magnetic field at the surface of the magnet is approximately 600 gauss.

In one embodiment, the magnetic pad is formed of a flexible binding material that is depressed into the central trough when the template surface is pressed against the lumbar region.

In one embodiment, the template surface is at an angle that matches the angle of the lumbar region of a wearer's torso.

In one embodiment, the angle is approximately 7 degrees.

In one embodiment, the magnetic pad matches the curvature of the spine vertebrae of a wearer and forms a magnetic field that floods the lumbar region of the wearer including five vertebrae L1, L2, L3, L4 and L5 and extends to S1 in the sacral region.

The foregoing and other objects, features and advantages of the invention will be apparent from the following detailed description in conjunction with the drawings.

BRIEF DESCRIPTION OF THE DRAWINGS

FIG. 19 depicts a pair of the magnets of the FIG. 17 type where each magnet is of the NSNSN magnet field configuration.

FIG. 20 depicts a schematic representation of the magnetic field in the XZ-plane direction of the magnet of FIG. 17.

FIG. 21 depicts a schematic representation of the magnetic field in a plane in the XZ-plane direction of the magnet of FIG. 17 in an expanded view offset from the support.

FIG. 22 depicts a schematic representation of the magnetic field in a plane in the YZ-plane direction of the magnet of FIG. 17 in an expanded view offset from the support.

FIG. 25 depicts a schematic representation of the magnetic field in the XZ-plane direction of each of the magnets of FIG. 24.

FIG. 26 depicts a front view of one of the magnets of FIG. 24.

FIG. 27 depicts a schematic representation of the magnetic field in the XZ-plane of the magnet of FIG. 26 in an expanded view offset from the support.

DETAILED DESCRIPTION

Figure 1:
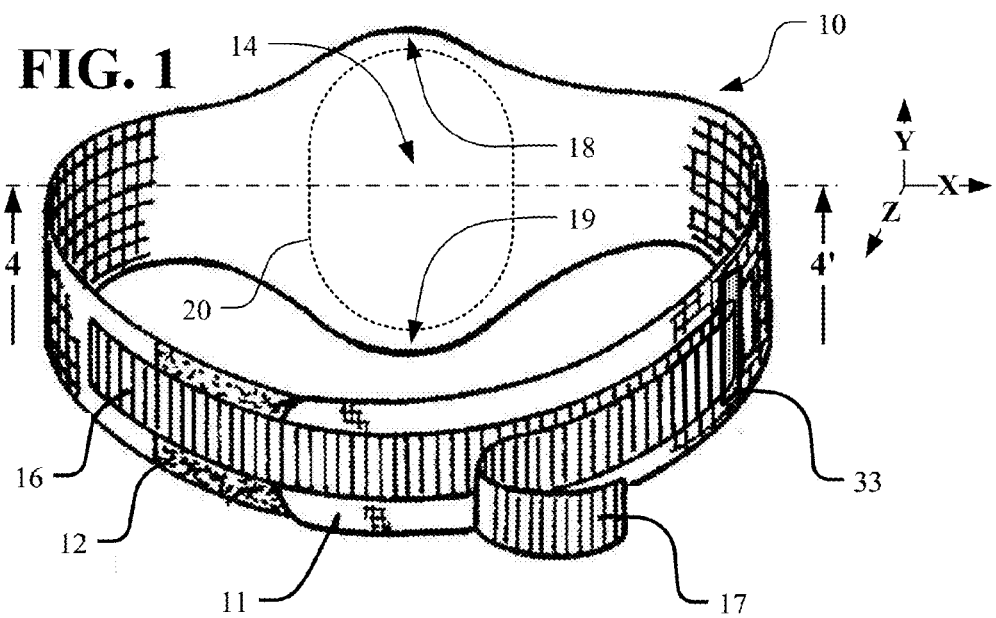
FIG. 1 is a perspective view illustrating an embodiment of an orthopedic support.

In FIG. 1, a perspective view is shown illustrating a first embodiment of a support 10. The support 10 has overlapping ends 11 and 12 and has a central region 14. In region 14, the edges of the support curve outwardly toward margins 18 and 19. The support 10 has a maximum width dimension in the region 14 and has a smaller width dimension at the ends 11 and 12. The two overlapping ends 11 and 12 are provided with complementary hook and eye fasteners in order to provide an adjustable closure for the support 10 about the torso of a user. A secondary closure is provided by support strap 16 having a width less than the width of ends 11 and 12. The support strap 16 extends over the ends 11 and 12 and has an end 17 that passes through a metal loop 33 and extends back over support strap 16. The top and bottom surfaces of the support strap 16 are provided with complementary hook and eye fasteners in order to provide an additional adjustable closure for the support 10. The end 17 is pulled against the loop 33 to secure the support 10 about the torso of a user and when tight is fastened with the hook and eye fasteners of the support strap 16. The support 10 is fabricated from any suitable material, such as a Nylon fabric, and is preferably a two-ply support secured around the perimeter so as to enable the retention therein of an orthopedic pad 20 in the region 14.

Figure 2:
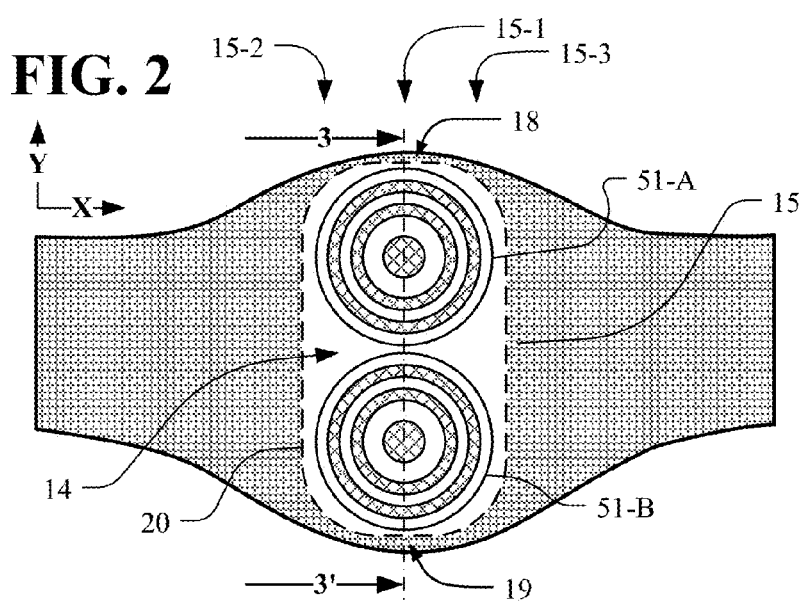
FIG. 2 is a front view of the surface of the orthopedic pad portion of the support of FIG. 1 with a cut away to show the circular magnets.

In FIG. 2, a front view of the surface of the orthopedic pad 20 in the region 14 of the support 10 of FIG. 1 is shown cut away to show the circular magnets 51-A and 51-B in the pad 20. In FIG. 2, the pad 20 in the region 14 of the support 10 is to be placed against the lower back region of a person wearing the support 10. The pad 20 in the region 14 is attached as part of the support 10.

In FIG. 2, the magnetic pad 20, including the magnets 51-A and 51-B, is flexible so that it contours to the surface of a user's back and to the underlying contoured template surface 15 of the support 10 when the support 10 is tightened around the torso of a user. The contoured template surface 15 has a transversely extending, parallel to the section line 3-3', central trough portion 15-1 for accommodating the protruding spinal processes of the wearer when the magnetic pad 20 is pressed against the lumbar region. The contoured template surface 15 has a transversely extending, parallel to the section line 3-3', pair of raised plateau regions 15-2 and 15-3 flanking the central trough portion 15-1 for contacting the erector spinae muscles of the wearer to provide support.

Figure 3:
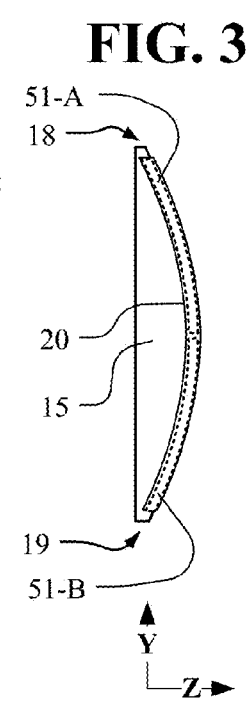
FIG. 3 is a section view taken along line 3-3' of FIG. 2.

In FIG. 3, a section view of the contoured template surface 15 taken along line 3-3' of FIG. 2 is shown. The magnetic pad 20, including the magnets 51-A and 51-B, is flexible so that it contours to the curved surface of template surface 15 between margins 18 and 19.

Figure 4:
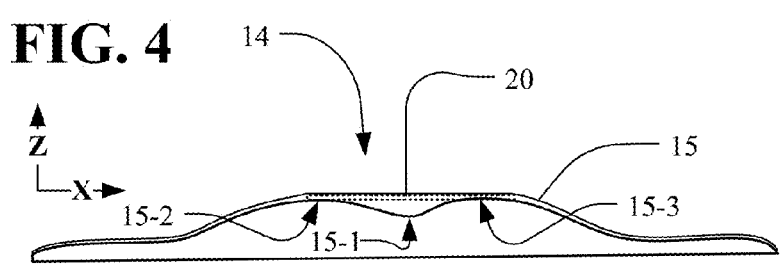
FIG. 4 is a section view taken along line 4-4' of FIG. 1.

In FIG. 4, a section view of the support 10 taken along line 4-4' of FIG. 1 is shown. The contoured template surface 15 has a transversely extending central trough portion 15-1. The contoured template surface 15 has a transversely extending pair of raised plateau regions 15-2 and 15-3 flanking the central trough portion 15-1. The magnetic pad 20 is glued or otherwise attached to the template surface 15 at the top of the raised plateau regions 15-2 and 15-3 so that the magnets 51-A and 51-B (see FIG. 2) are over the central trough portion 15-1. Because the magnetic pad 20 and the magnets 51-A and 51-B (see FIG. 2) are flexible, the magnetic pad 20 and the magnets 51-A and 51-B conform to the contoured template surface 15 and depress into the over the central trough portion 15-1. In FIG. 4, the magnetic pad 20 and the magnets 51-A and 51-B, attached at the top of of the raised plateau regions 15-2 and 15-3, is depressed into the trough portion 15-1 to assume the shape of the contoured template surface 15 when the support 10 is pressed against the lumbar region of a wearer.

Figure 5:
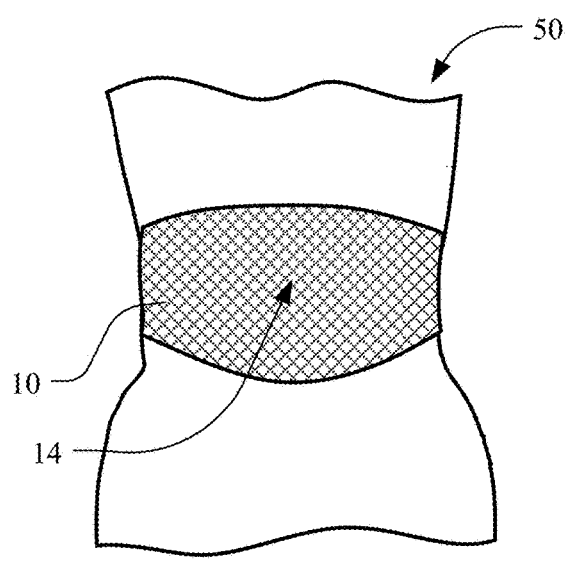
FIG. 5 depicts a back view of a person's torso wearing the support of FIG. 1.

In FIG. 5, a back view of a person's torso 50 is shown wearing the support 10 of FIG. 1. The region 14 has a back side that faces outward away from the torso 50 with the magnets 51-A and 51-B of FIG. 2 facing inward toward the torso 50 and positioned against the lower back portion of the torso 50.

Figure 6:
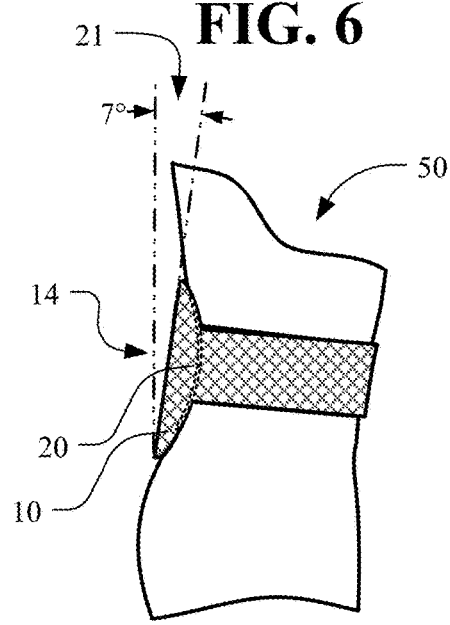
FIG. 6 depicts a side view of a person's torso wearing the support of FIG. 1.

In FIG. 6, a side view of a person's torso 50 is shown wearing the support 10 of FIG. 1. The region 14 has a back side that faces outward away from the torso 50 with the magnets 51-A and 51-B of FIG. 2 facing inward toward the torso 50 and positioned against the lower back portion of the torso 50. The support 10 is positioned about the waist of the user's torso 50 at an angle 21, which typically is about 7 degrees from a vertical line. The template surface of the magnetic pad 20, including the trough 15-1 and the raised plateau regions 15-2 and 15-3 (see FIG. 4), rests against the wearer's back in the lower back region. The plateau regions 15-2 and 15-3 make surface contact with the erector spinae muscles of the wearer through the skin, and the central hollow trough 15-1 accommodates the bony protrusions of the spine. The magnetic pad 20 responds to extension of the back away from the idealized posture represented by the template surface of magnetic pad 20 by opposing such extension away from the idealized posture in response to the relative stiffness of the magnetic pad 20 material. The lower back has a natural tendency to adapt to and follow the smooth surface of the magnetic pad 20 which guides the lower back into ideal posture.

Figure 7:
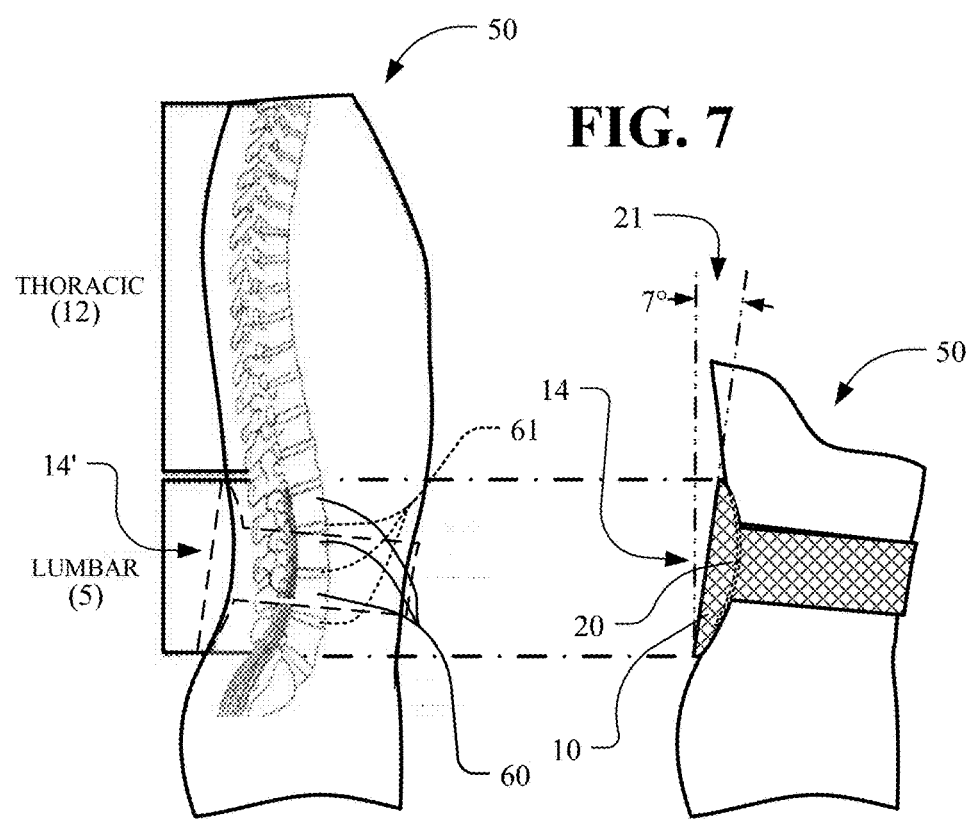
FIG. 7 depicts a side view of a person's torso wearing the support of FIG. 1 and showing how the support aligns with the lumbar region of the person's spine.

In FIG. 7, a side view of a person's torso wearing the support 10 of FIG. 1 is shown, with the same view as in FIG. 6, and additionally showing how the support 10 and the magnetic pad 20 align with the lumbar region and the spine of the torso 50. The torso 50 includes the thoracic region with twelve vertebrae and the lumbar region with five vertebrae. The location and orientation of the support 10 is shown by a dotted line superimposed over the skeleton portion of the lumbar region. The support 10 is positioned about the waist of the user's torso 50 at an angle 21, which typically is about 7 degrees which generally matches the angle of the lumbar region 14' of the user's torso. The vertebrae 60 are separated by disks 61. The lumbar region 14' of the user's torso additionally includes muscles, tendons, skin and other body components not shown but which contribute to the movement and function of the lumbar region and which can suffer from poor spinal mechanics.

Figure 8:
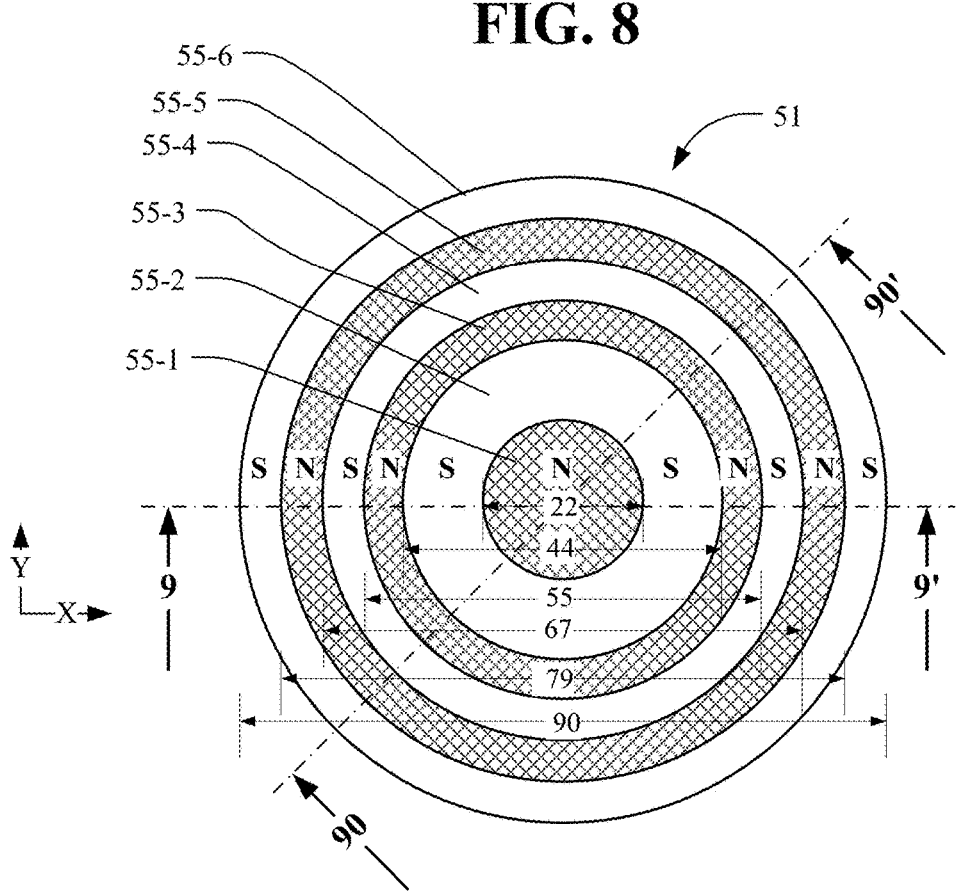
FIG. 8 depicts a top view of one of the magnets used in the support of FIG. 1 having a SNSNSNSNSNS magnetic field configuration.

In FIG. 8, a top view of the magnet 51 is shown and is representative of one of the magnets used in the support 10 of FIG. 1, for example, magnets 51-A and 51-B in FIG. 2. The magnet 51 is a Concentric Circle Magnet manufactured by BIOflex Medical Magnets, Inc. and has properties described in U.S. Pat. No. 7,611,453 entitled APPARATUS AND METHOD FOR STATIC MAGNETIC FIELD TREATMENT OF TISSUE, ORGANS, CELLS, AND MOLECULES.

The magnet 51 in the top view is circular and includes the concentric circular regions 55-1, 55-2, 55-3, 55-4, 55-5 and 55-6 which have polarities, indicated by north (N) and south (S), of SNSNSNSNSNS when viewed across a major axis such as section line 9-9'. The concentric circular regions (partitions) 55-1, 55-2, 55-3, 55-4, 55-5 and 55-6 have diameters that can vary widely. In FIG. 8, the concentric circular regions (partitions) 55-1, 55-2, 55-3, 55-4, 55-5 and 55-6 have diameters 22 mm, 44 mm, 55 mm, 67 mm, 79 mm and 90 mm, respectively. These diameters are for the concentric circular regions in the magnet of FIG. 8 and are only by way of example and many other diameters can be employed. In general, the diameters together with other parameters correlate to the depth of penetration of the magnetic field into the lumbar region of a body, to the strength of the magnetic field, the location of the magnetic field and the direction of the magnetic field.

Figure 9:
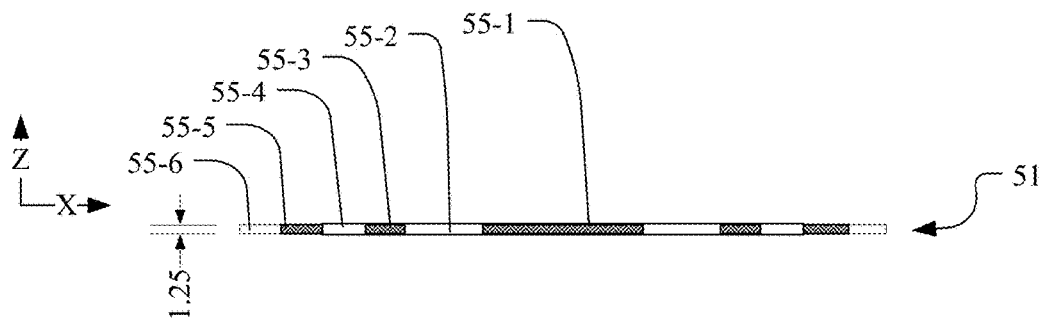
FIG. 9 depicts a front view of the magnet of FIG. 8.

In FIG. 9, a front view is shown of the magnet 51 of FIG. 8. The magnet 51 includes a layer 51 formed of concentric rings. In the embodiment of FIG. 8, the magnet 51 has a thickness of approximately 1.5 millimeters (mm). The thickness for producing magnets in general is not critical and can vary. The thickness for use in the orthopedic support 10 needs to be thin enough to permit the magnetic pad 20 to conform to the curvature of the trough 15-1 and the raised plateau regions 15-2 and 15-3 as discussed in connection with FIG. 2 and FIG. 4. In the FIG. 9 embodiment, the layer 51 is 1.5 mm thick.

Figure 10:
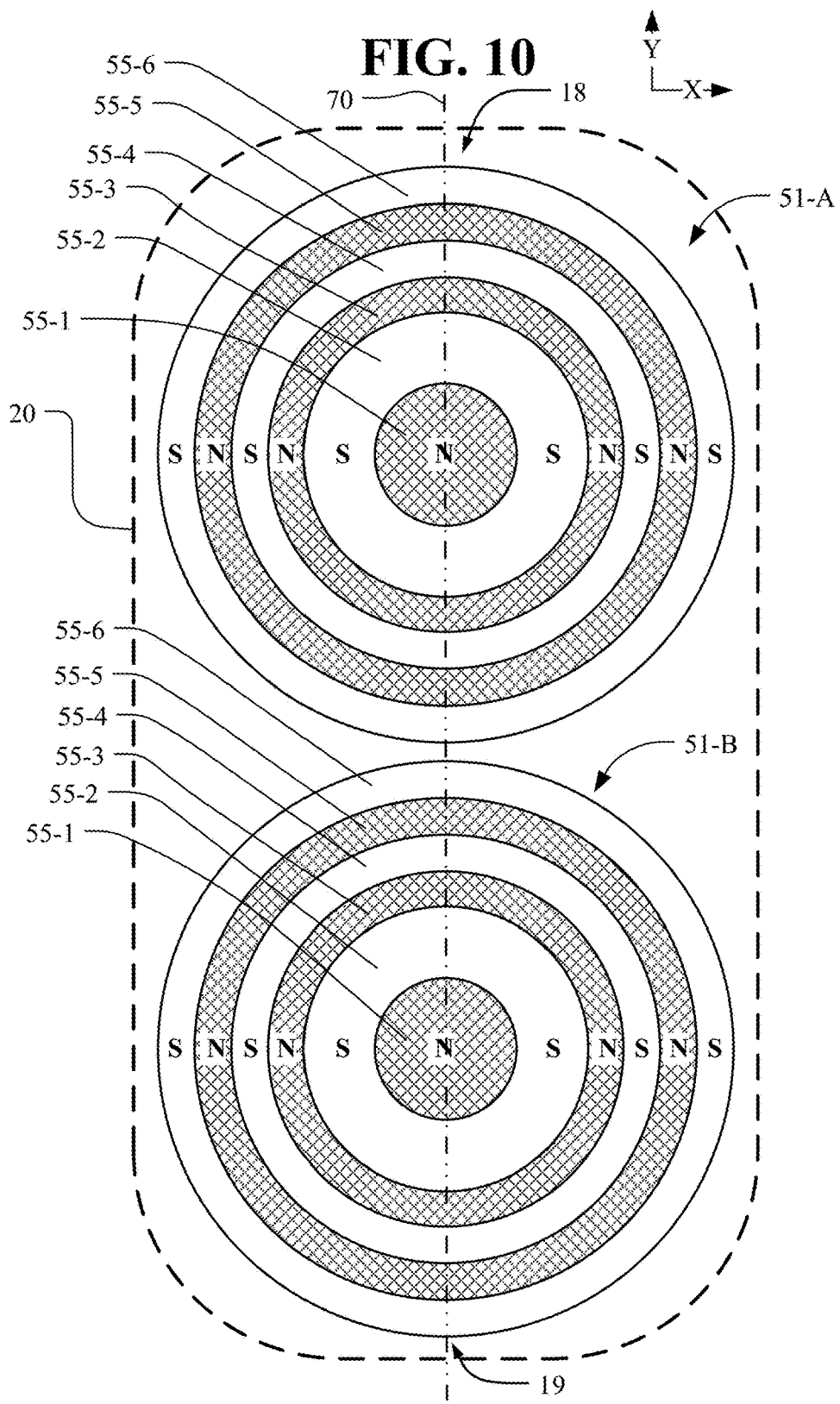
FIG. 10 depicts a pair of the magnets of the FIG. 1 type where each magnet is of the SNSNSNSNSNS magnetic field configuration.

In FIG. 10, two magnets 51-A and 51-B of the FIG. 8 and FIG. 9 type are shown imbedded in the magnetic pad 20. The magnets 51-A and 51-B both include the concentric circle polarity orientation SNSNSNSNSNS. In alternate embodiments, either one or both of the magnets 51-A and 51-B have the polarities reversed replacing all the N's with S's and all the S's with N's to form a concentric circle polarity orientation NSNSNSNSNSN. The magnets 51-A and 51-B are arranged in the magnetic pad 20 which is more than 189 mm high by more than 90 mm wide so as to contain the 90 mm wide magnets 51-A and 51-B. The thickness of the pad 20, as indicated by the magnet thickness in FIG. 9, is approximately 1.5 mm. The magnetic pad 20 and the magnets 51-A and 51-B can have smaller and larger sizes and the dimensions given are by way of example. In FIG. 10, the first and second magnets 51-A and 51-B are juxtaposed and the first and second magnets 51-A and 51-B are each centered on a line 70 between the upper margin 18 and the lower margin 19. In general, the dimensions are selected so that a magnetic field is produced that floods the lumbar region of the wearer including five vertebrae L1, L2, L3, L4 and L5 and extending to S1 in the sacral region.

Figure 11:
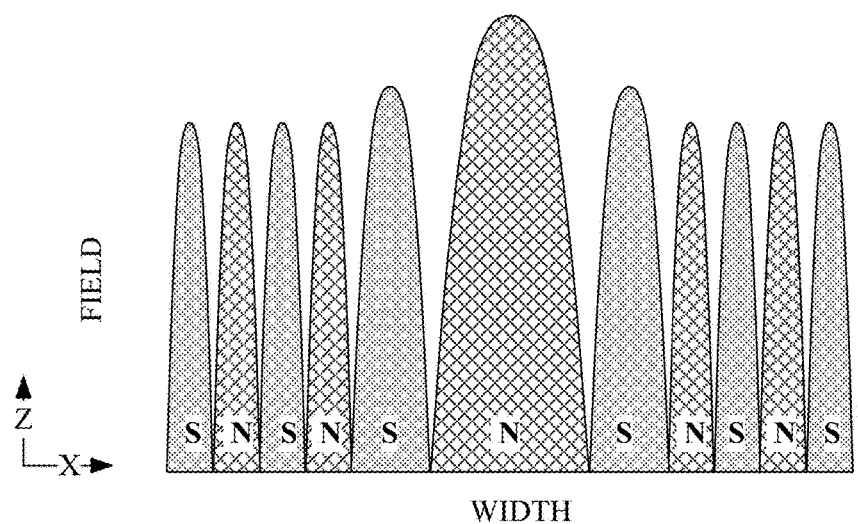
FIG. 11 depicts a schematic representation of the magnetic field in the XZ-plane direction of the magnet of FIG. 8.

In FIG. 11, a schematic representation of the magnetic field in the XZ-plane for the magnet of FIG. 8 and FIG. 9 is shown. The magnetic field is viewed when taken along a central section line such as section line 9-9' in FIG. 8 and extends in the positive Z-axis direction in FIG. 9 in the XZ-plane. The section line 9-9' in FIG. 8 is defined to be at 0 degrees. If another section line, for example section line 90-90' at 45 degrees is taken, the cross section again appears as shown in FIG. 11. It is apparent that the concentric circle magnets form a magnetic field that is represented by multiple conic sections with alternating North (N) and South (S) polarities. When these multiple conic section alternating North (N) and South (S) polarities flood the lumbar region with a magnetic field strength having a therapeutic value, a beneficial therapeutic result occurs.

In FIG. 11, the WIDTH axis corresponds to the 90 mm width of the magnet 51 of FIG. 8. In FIG. 11, the FIELD axis corresponds to the field that is directed into the lumbar region in the positive Z-axis direction by the support 10 of FIG. 1. Although the magnet of FIG. 8 also generates a magnetic field in the negative Z-axis direction, that field in the negative Z-axis direction is not shown in FIG. 11 since it is directed away from the body, has no therapeutic effect and therefore is ignored.

Figure 12:
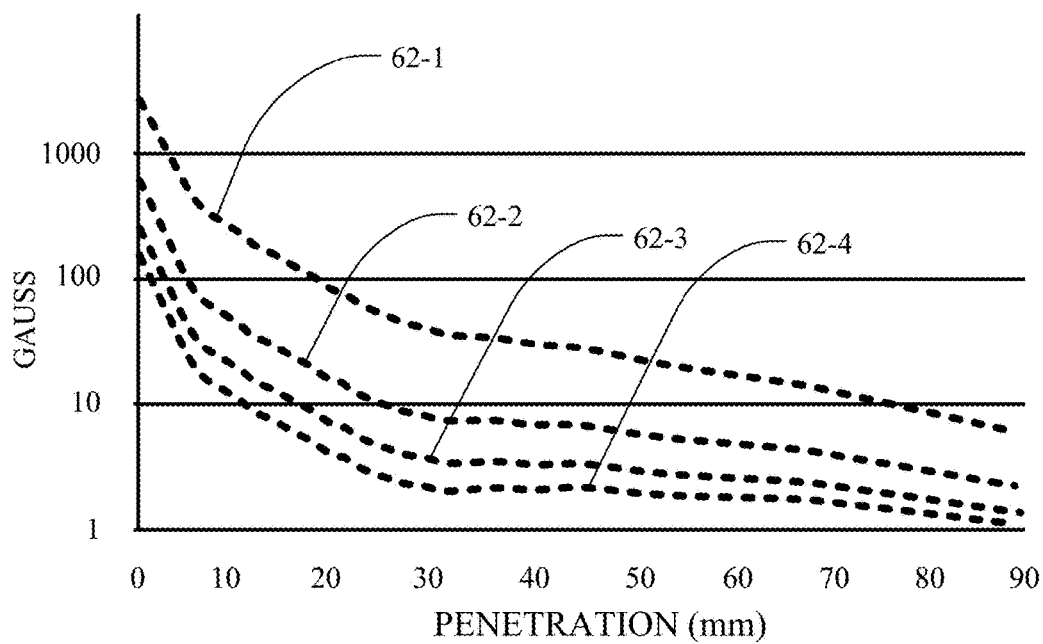
FIG. 12 depicts a representation of the magnetic field strengths of various magnets and the penetration depth when the magnets are used in an orthopedic support.

In FIG. 12, a representation of the magnetic field strengths of various magnets and the penetration depth of those fields when the magnets are used in an orthopedic support is shown. The concentric circular magnets tend to have a field pattern that is high at the surface where the support contacts the body (0 mm penetration) and tends to be more flat from the 30 mm (1.2 inch) depth to the 60 mm (2 inch) depth of penetration and beyond. In FIG. 12, the curves 62-1, 62-2, 62-3 and 62-4 represent different magnetic strengths of concentric circular magnets. The 0 mm penetration levels for the curves 62-1, 62-2, 62-3 and 62-4 are 1200 gauss, 600 gauss, 500 gauss and 110 gauss, respectively. The magnetic field gauss level and the field pattern of the concentric circular magnets in the pad 20 is controlled to insure the desired gauss level penetration into the lumbar region. A wide range of amplitudes for the magnetic fields of FIG. 12 are possible from 1 to more than 6000 gauss.

In one preferred embodiment, the magnetic pad 20 is a flexible pad made from poly-carbonate or other binding material. In manufacture, the binding material is heated and mixed with ferrite powder and/or other magnetic powders. The mixture is rolled into a thin flexible sheet and cooled to form a magnetizable sheet. Magnetic fields are applied to the magnetizable sheet to form the concentric circle partitions 55-1, 55-2, 55-3, 55-4, 55-5 and 55-6 for magnet 51-A and for magnet 51-B. The magnetic powers and magnetization steps provide the gauss strength and penetration characteristics which permit the magnetic fields from the magnets 51-A and 51-B to penetrate the lumbar region and reach tissues and surrounding regions that can benefit from the magnetic field produced. The composition of and the quantity of the ferrite powder and/or other magnetic powders is used to help control the gauss strength and penetration characteristics of the pad 20.

Figure 13:
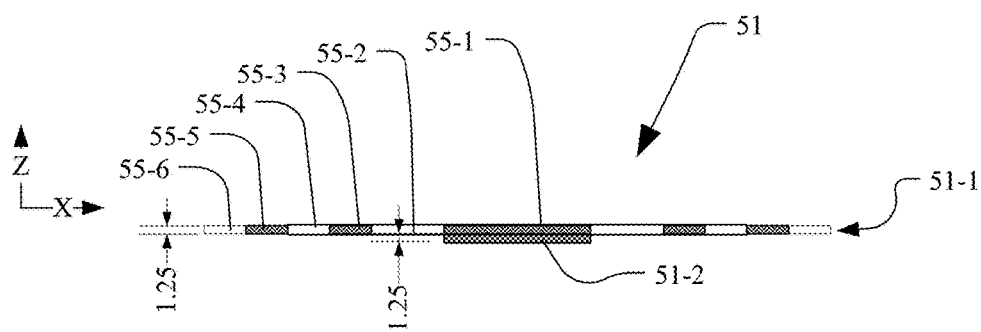
FIG. 13 depicts a front view of an alternate embodiment of the magnet of FIG. 8 including an additional linear magnet in the center.

In FIG. 13, a front view of an alternate embodiment of the magnet 51 of FIG. 8 is shown including an additional linear magnet 51-2 in the center in a second layer under the layer 51-1 and under and the same size as the circle partition 55-1. In one embodiment, the 0 mm penetration level of FIG. 11 for the magnet 51 of FIG. 8 is 500 gauss. The addition of the linear magnet 51-2, increases the 0 mm penetration level of FIG. 11 for the combined magnet 51 including layers 55-1 and 51-2 of FIG. 13 is 600 gauss. In the embodiment of FIG. 13, each of the layers 51-1 and 51-2 is 1.25 mm thick.

In FIG. 13, the magnet 51 includes an upper layer 51-1 formed by concentric rings and includes a bottom layer 51-2 formed by a single axial magnet. The upper layer 51-1 includes cross sections of the concentric circle partitions 55-1, 55-2, 55-3, 55-4, 55-5 and 55-6 of FIG. 8. In FIG. 13, the ring sections 55-1, 55-3 and 55-5 have a North-South (NS) orientation where North (N) is toward the top of the drawing page in the positive Z-axis direction and South (S) is toward the bottom of the drawing page in the negative Z-axis direction. The ring sections 55-2, 55-4 and 55-6 have a South-North (SN) orientation. The bottom layer 51-2 is formed as a single axial magnet having a North-South (NS) orientation where North (N) is toward the top of the drawing page in the positive Z-axis direction and South (S) is toward the bottom of the drawing page in the negative Z-axis direction. If viewed from the top, the layer 51-2 would appear as a continuous 90 mm circle with the entire top having a North polarization. If viewed from the bottom, the layer 51-2 would appear as a continuous 90 mm circle with the entire bottom having a South polarization.

Figure 14:
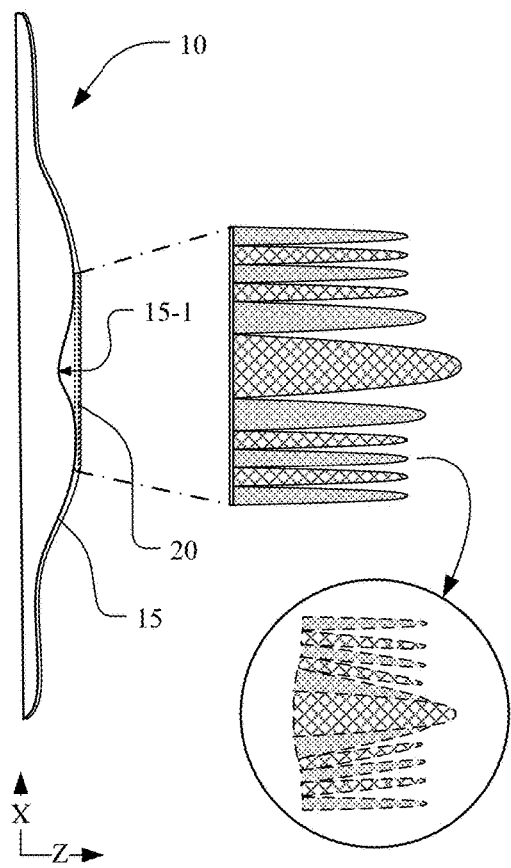
FIG. 14 depicts a schematic representation of the magnetic field in a plane in the XZ-plane direction of the magnet of FIG. 8 in an expanded view offset from the support.

In FIG. 14, a schematic representation of a section of the magnetic field in the XZ-plane of the magnet of FIG. 13 is shown in an expanded view offset from the support 10 and the pad 20. The magnetic field in the XZ-plane of FIG. 14 is a section view taken along the section line 4-4' in FIG. 1. In FIG. 14, the support 10 and pad 20 are not pressed against a user and hence the pad 20 is not depressed into the trough 15-1 and the field pattern is as shown in FIG. 11. When the pad 20 is depressed into the trough 15-1, the field pattern is changed as shown in the circle in FIG. 11. Although the field is somewhat altered by depression into the trough 15-1 as shown in the circle in FIG. 14, the efficacy of the magnetic field is not materially altered and still tends to flood the lumbar region.

Figure 15:
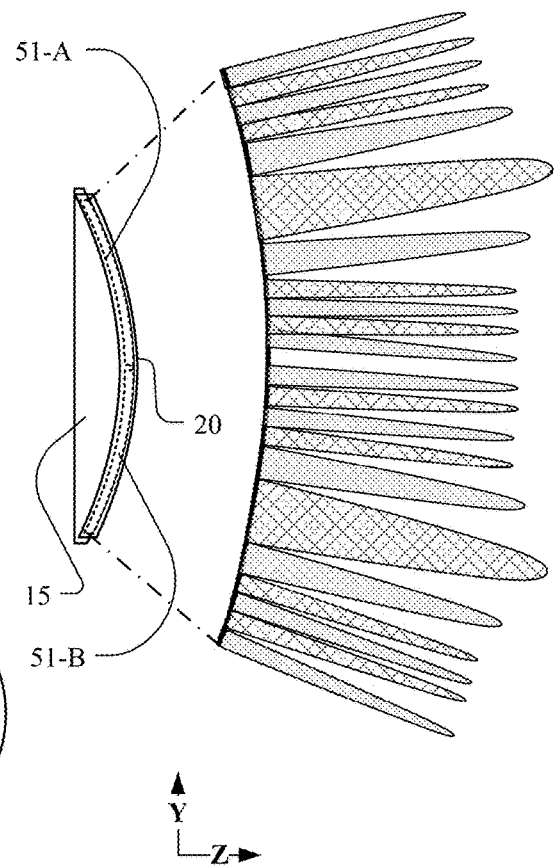
FIG. 15 depicts a schematic representation of the magnetic field in a plane in the YZ-plane direction of the magnet of FIG. 8 in an expanded view offset from the support.

In FIG. 15, a schematic representation of the magnetic field in the YZ-plane of the magnet of FIG. 13 is shown in an expanded view offset from the contoured template surface 15 and the pad 20. The magnetic field in the YZ-plane of FIG. 15 is a section view taken along the section line 3-3' in FIG. 2. In FIG. 15, the pad 20 conforms to the curvature of the contoured template surface 15 and emanates from the magnets 51-A and 51-B.

Figure 16:
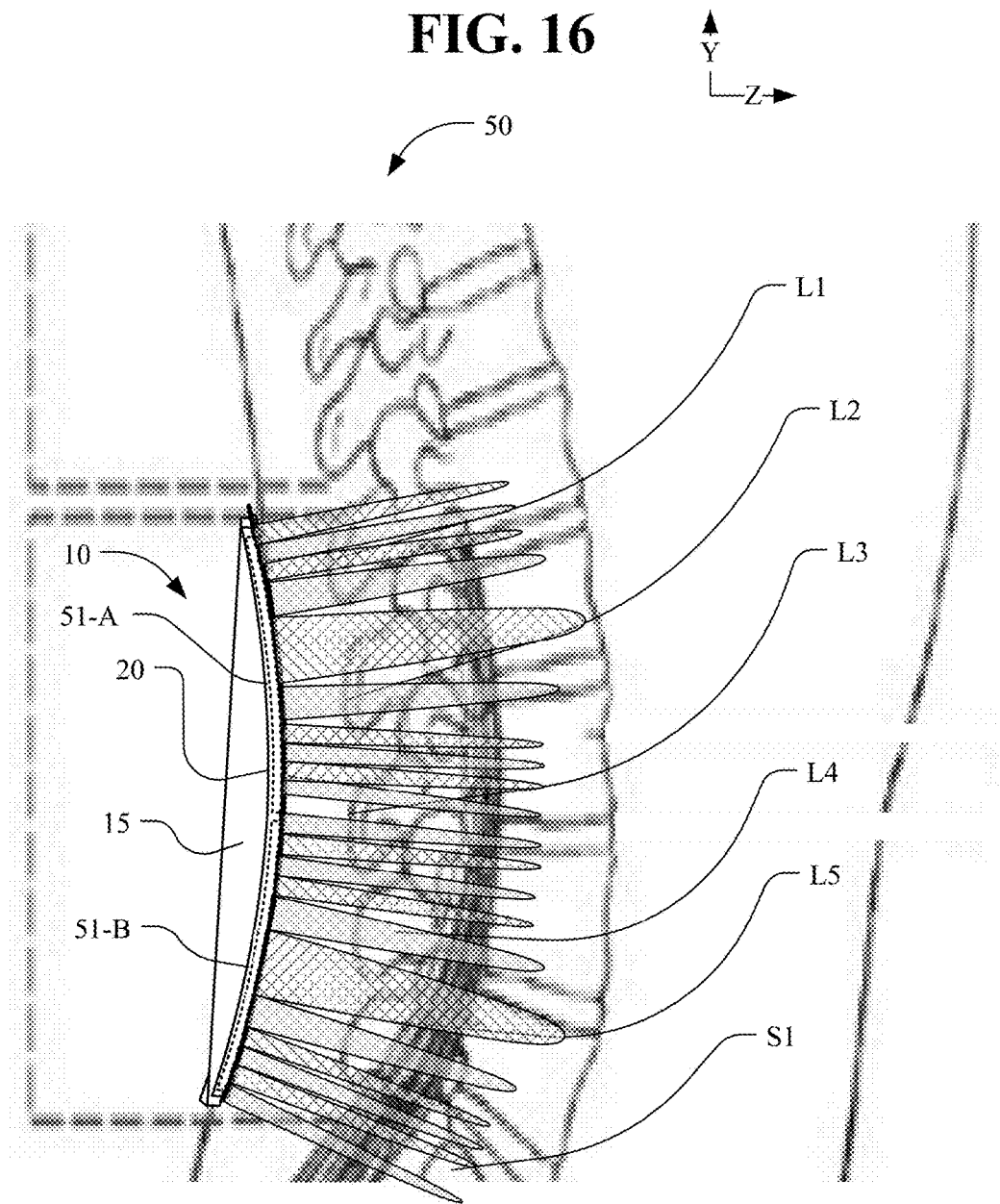
FIG. 16 depicts a schematic representation of the support positioned as shown in FIG. 7 with a magnetic field, shown in a plane in the YZ-plane direction, of the magnet of FIG. 8.

In FIG. 16, a schematic representation of the a template surface 15 as shown in FIG. 3 of the support 10 is positioned as shown in FIG. 7 with a magnetic field section along section line 3-3' in FIG. 2, shown in the YZ-plane, for the magnets of FIG. 10. The magnetic field from the magnets 51-A and 51-B of the support 10 extends into the lumbar region and the sacral region where the curvature of the pad 20 and the magnets 51-A and 51-B matches the curvature of the spine vertebrae. The lumbar region includes the five vertebrae L1, L2, L3, L4 and L5 between the rib cage and the pelvis and extends to S1 in the sacral region. These vertebrae are the largest segments of the vertebral column and are characterized by the absence of the foramen transversarium and facets on the sides of the body. The strength of the field into the lumbar region is as described in connection with FIG. 12. The sacral region includes S1, S2, S3, S4 and S5 where S1 is next after L5.

Figure 17:
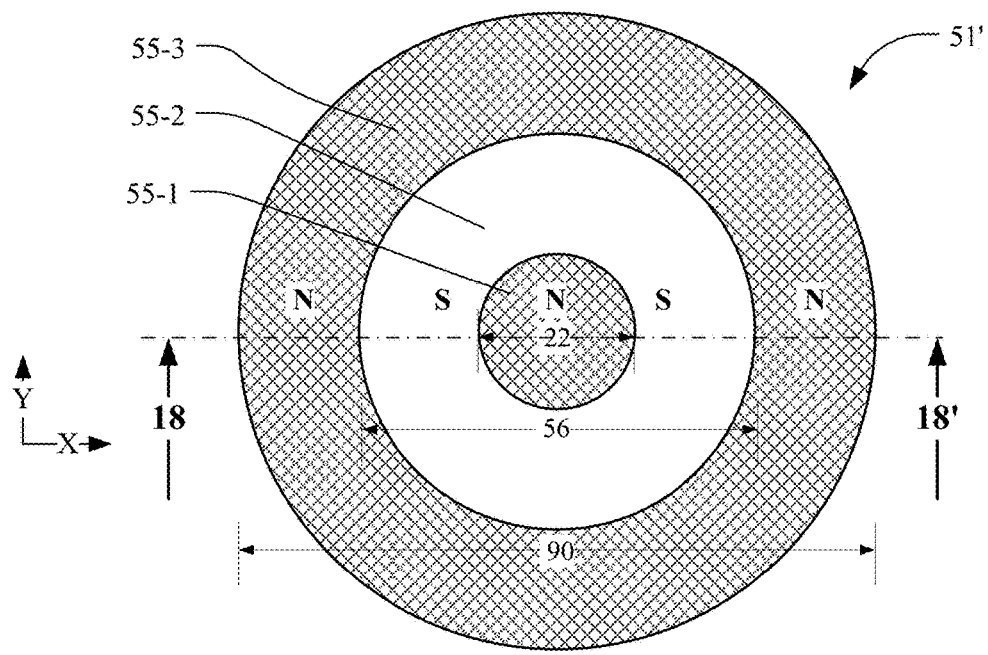
FIG. 17 depicts a top view of one of the magnets used in the support of FIG. 1 having a NSNSN magnetic field configuration.

In FIG. 17, a top view of the magnet 51' is shown and is representative of one of the magnets used in an alternate embodiment of the support 10 of FIG. 1. The magnet 51' of FIG. 17 is alternate embodiment of the magnets 51-A and 51-B in FIG. 2. The magnet 51' is a Concentric Circle Magnet. The magnet 51' in the top view is circular and includes the concentric circular regions 55-1, 55-2 and 55-3 which have polarities, indicated by north (N) and south (S), of NSNSN when viewed across a major axis such as section line 18-18' in FIG. 17. The concentric circular regions (partitions) 55-1, 55-2 and 55-3 have diameters that can vary widely. In FIG. 17, the concentric circular regions (partitions) 55-1, 55-2 and 55-3 have diameters 22 mm, 56 mm and 90 mm, respectively. In general, the diameters together with other parameters correlate to the depth of penetration of the magnetic field into the lumbar region of a body, to the strength of the magnetic field, the location of the magnetic field and the direction of the magnetic field.

Figure 18:
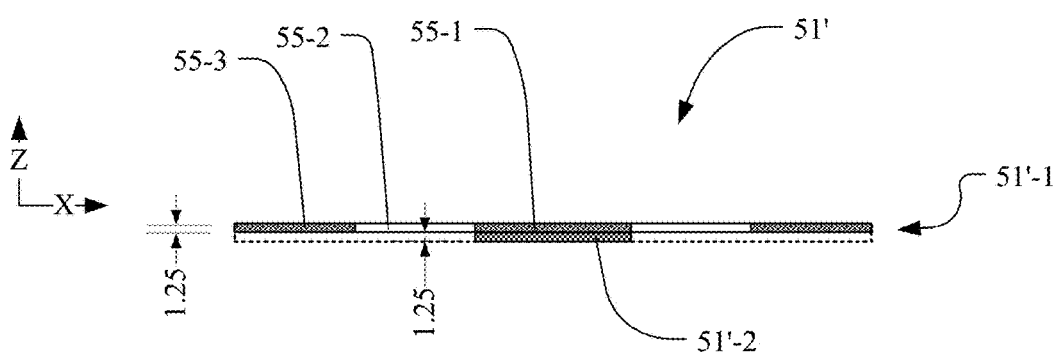
FIG. 18 depicts a front view of the magnet of FIG. 17.

In FIG. 18, a front view is shown of the magnet 51' of FIG. 17. The magnet 51' of FIG. 18 includes a concentric circle magnet 55-1 in a first layer 51'-1 and an additional circular linear magnet under and the same size as magnet 55-1 in a second layer 51'-2. The first layer 51'-1 includes the concentric circular regions 55-1, 55-2 and 55-3. The linear magnet in layer 51'-2 is located juxtaposed the center concentric magnet 55-1. In one embodiment, the 0 mm penetration level of FIG. 12 for the magnet 51' of FIG. 18 is 600 gauss where the penetration in one example is typically like that of curve 62-2 in FIG. 12. In FIG. 18, the layer 51'-1 has a thickness of approximately 1.25 millimeters (mm) and the layer 51'-2 has a thickness of approximately 1.25 millimeters (mm). The thickness for producing magnets can vary. The thickness for use in the orthopedic support 10 needs to be thin enough to permit the magnetic pad 20 to conform to the curvature of the trough 15-1 and the raised plateau regions 15-2 and 15-3 as discussed in connection with FIG. 2 and FIG. 4. In the FIG. 18 embodiment, the magnet 51' is 2.5 mm thick.

In FIG. 19, two magnets 51'-A and 51'-B of the FIG. 17 and FIG. 18 type are shown imbedded in the magnetic pad 20. The magnets 51'-A and 51'-B both include the concentric circle polarity orientation NSNSN. In alternate embodiments, either one or both of the magnets 51'-A and 51'-B have the polarities reversed replacing all the N's with S's and all the S's with N's to form a concentric circle polarity orientation SNSNS. The magnets 51'-A and 51'-B are arranged in the magnetic pad 20 which is more than 189 mm high by more than 90 mm wide so as to contain the 90 mm wide magnets 51'-A and 51'-B. The thickness of the pad 20, as indicated by the magnet thickness in FIG. 18, is approximately 2.5 mm. The magnetic pad 20 and the magnets 51'-A and 51'-B can have smaller and larger sizes and the dimensions given are by way of example. In FIG. 19, the first and second magnets 51'-A and 51'-B are juxtaposed and the first and second magnets 51'-A and 51'-B are each centered on a line 70 between the upper margin 18 and the lower margin 19. In general, the dimensions are selected so that a magnetic field is produced that floods the lumbar region of the wearer including five vertebrae L1, L2, L3, L4 and L5 and extending to S1 in the sacral region.

In FIG. 20, a schematic representation of the magnetic field in the XZ-plane for the magnet of FIG. 17 and FIG. 18 is shown. The magnetic field is viewed when taken along a central section line such as section line 18-18' in FIG. 17. In FIG. 20, the WIDTH axis corresponds to the 90 mm width of the magnet 51' of FIG. 17. In FIG. 20, the FIELD axis corresponds to the field that is directed into the lumbar region in the positive Z-axis direction by the support 10 of FIG. 1. Although the magnet of FIG. 17 also generates a magnetic field in the negative Z-axis direction, that field in the negative Z-axis direction is not shown in FIG. 20 since it is directed away from the body, has no therapeutic effect and therefore is ignored. In FIG. 20, the magnetic field strengths of various magnets and the penetration depth of those fields when the magnets are used in an orthopedic support is like that shown and described in connection with FIG. 12. The concentric circular magnets tend to have a field pattern that has a magnitude that is high at the surface where the support contacts the body (0 mm penetration) and tends to be more flat from the 30 mm (1.2 inch) depth to the 60 mm (2 inch) depth of penetration and beyond. In FIG. 12, the curves 62-1, 62-2, 62-3 and 62-4 represent different magnetic strengths of concentric circular magnets. The 0 mm penetration levels for the curves 62-1, 62-2, 62-3 and 62-4 are 1200 gauss, 600 gauss, 500 gauss and 110 gauss, respectively. The gauss level and the field pattern of the concentric circular magnets in the pad 20 is controlled to insure the desired gauss level penetration into the lumbar region.

In one preferred embodiment, the magnetic pad 20 is a flexible pad made from poly-carbonate or other binding material. In manufacture, the binding material is heated and mixed with ferrite powder and/or other magnetic powders. The mixture is rolled into a thin flexible sheet and cooled to form a magnetizable sheet. Magnetic fields are applied to the magnetizable sheet to form the concentric circle partitions 55-1, 55-2 and 55-3 for magnet 51'-A and for magnet 51'-B. The magnetic powers and magnetization steps provide the gauss strength and penetration characteristics which permit the magnetic fields from the magnets 51'-A and 51'-B to penetrate the lumbar region and reach tissues and surrounding regions that can benefit from the magnetic field produced. The composition of and the quantity of the ferrite powder and/or other magnetic powders is used to help control the gauss strength and penetration characteristics of the pad 20.

In FIG. 21, a schematic representation of a section of the magnetic field in the XZ-plane of the magnet of FIG. 17 is shown in an expanded view offset from the support 10 and the pad 20. The magnetic field in the XZ-plane of FIG. 21 is a section view taken along the section line 4-4' in FIG. 1. In FIG. 21, the support 10 and pad 20 are not pressed against a user and hence the pad 20 is not depressed into the trough 15-1 and the field pattern is as shown in FIG. 20. When the pad 20 is depressed into the trough 15-1, the field pattern is changed as shown in the circle in FIG. 21. Although the field is somewhat altered by depression into the trough 15-1 as shown in the circle in FIG. 21, the efficacy of the magnetic field is not materially altered and tends to flood the lumbar region.

In FIG. 22, a schematic representation of the magnetic field in the YZ-plane of the magnet of FIG. 17 is shown in an expanded view offset from the contoured template surface 15 and the pad 20. The magnetic field in the YZ-plane of FIG. 22 is a section view taken along the section line 3-3' in FIG. 2 when the magnets 51'-A and 51'-B and the pad 20 of FIG. 19 are used in FIG. 2. In FIG. 22, the pad 20 conforms to the curvature of the contoured template surface 15 and emanates from the magnets 51'-A and 51'-B.

Figure 23:
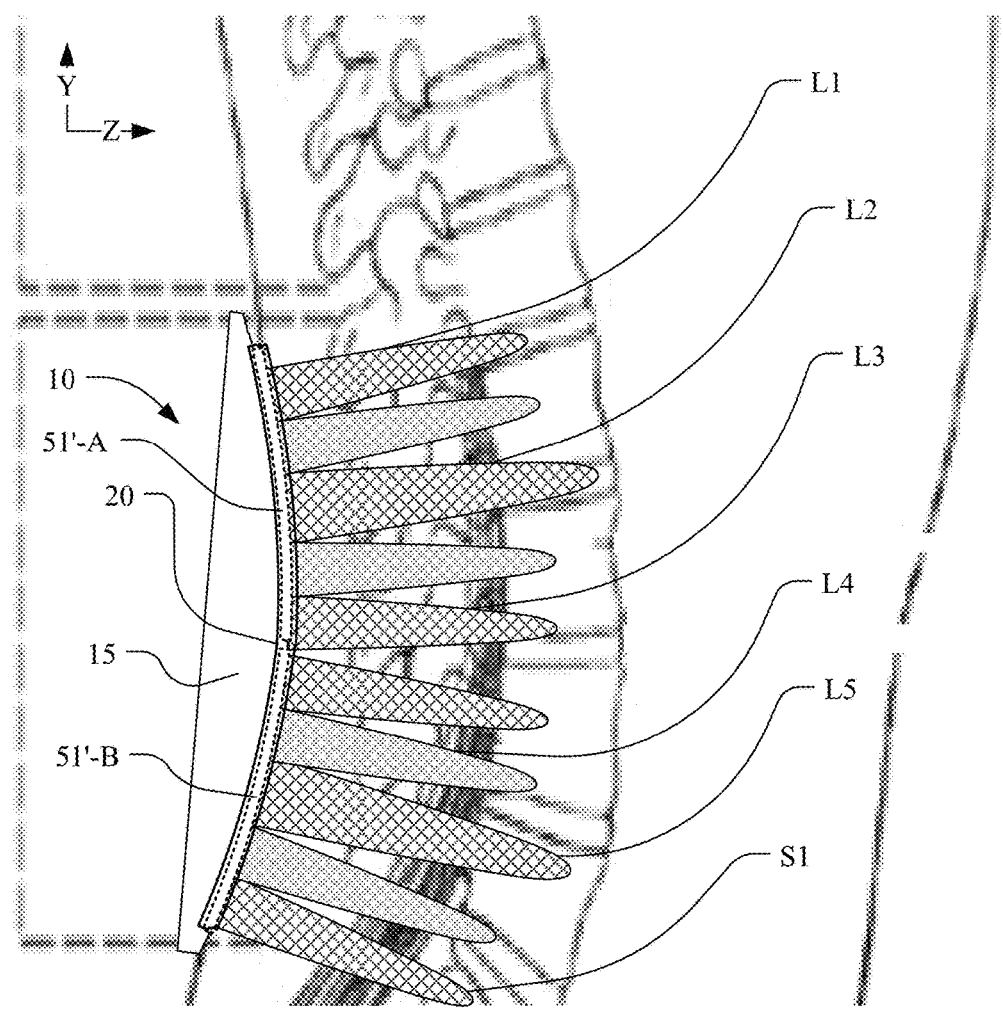
FIG. 23 depicts a schematic representation of the support positioned as shown in FIG. 7 with a magnetic field, shown in a plane in the YZ-plane direction, of the magnet of FIG. 17.

In FIG. 23, a schematic representation of the a template surface 15 as shown in FIG. 3 is positioned as shown in FIG. 7 with a magnetic field section along section line 3-3' in FIG. 2, shown in the YZ-plane, when the magnets 51'-A and 51'-B and the pad 20 of FIG. 19 are used in FIG. 2. The magnetic field from the magnets 51'-A and 51'-B extends into the lumbar region and the sacral region where the curvature of the pad 20 and the magnets 51'-A and 51'-B matches the curvature of the spine vertebrae. The lumbar region includes the five vertebrae L1, L2, L3, L4 and L5 between the rib cage and the pelvis and extends to S1 in the sacral region. These vertebrae are the largest segments of the vertebral column and are characterized by the absence of the foramen transversarium and facets on the sides of the body. The strength of the field is as described in connection with FIG. 12. The sacral region includes S1, S2, S3, S4 and S5 where S1 is next after L5.

Figure 24:
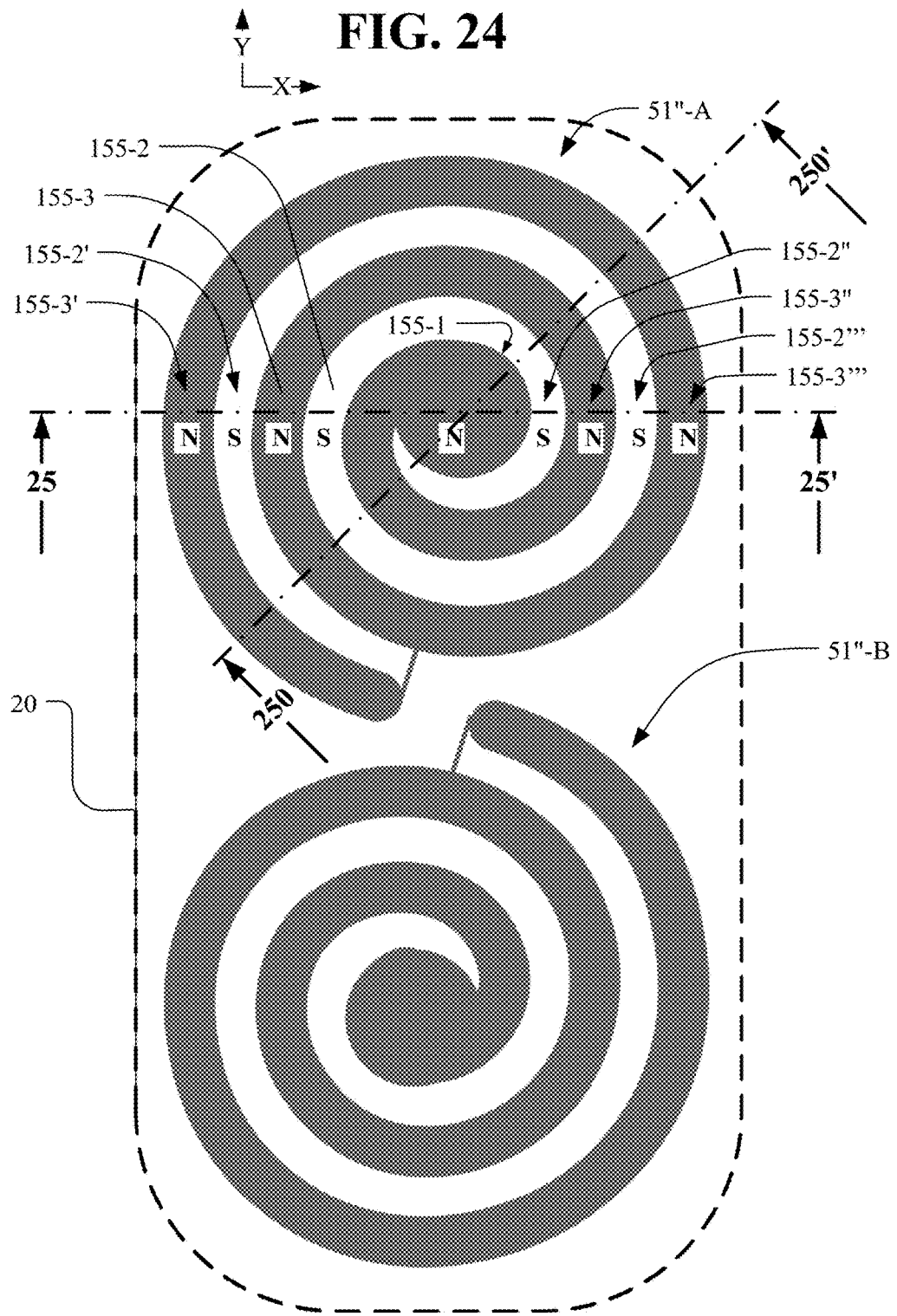
FIG. 24 depicts a top view of a pair of the magnets used in the support of FIG. 1 where each magnet is of the NSNSNSNSN magnetic field configuration.

In FIG. 24, a pair of the magnets 51"-A and 51"-B are shown where each magnet is of the NSNSNSNSN magnetic field configuration. The magnet 51"-A in the top view is helical and includes the helical regions 155-1, 155-2 and 155-3 which have alternating polarities, indicated by north (N) and south (S), of NSNSNSNSN when viewed across a major axis such as section line 25-25'. The alternating polarities, indicated by north (N) and south (S), are essentially the same when viewed across other of the major axis center lines such as section line 250-250'. In FIG. 24, the region 155-1 includes a circle having a diameter of 22 mm. The regions 155-2 and 155-3 have widths of approximately 8 mm. The overall width of each of the magnets 51"-A and 51"-B is in one typical embodiment 90 mm. These dimensions are by way of example and the overall width and the dimensions of the regions 155-1, 155-2 and 155-3 can vary widely. When viewed along the major center line 25-25', the regions 155-2 and 155-3 cross the center line at locations 155-3', 155-2', 155-3, 155-2, 155-1, 155-2", 155-3", 155-2''' and 155-3'''.

In FIG. 25, a schematic representation of the magnetic field in the XZ-plane direction of each of the magnets 51"-A and 51"-B of FIG. 24. In FIG. 25, the WIDTH axis corresponds to the 90 mm width of the magnet 51 of FIG. 8. In FIG. 25, the FIELD axis corresponds to the field that is directed into the lumbar region in the positive Z-axis direction by the support 10 of FIG. 1. Although the magnets of FIG. 24 also generate a magnetic field in the negative Z-axis direction, that field in the negative Z-axis direction is not shown in FIG. 24 since it is directed away from the body, has no therapeutic effect and therefore is ignored.

In FIG. 26, a sectional front view of the magnet 51"-A of FIG. 24 is shown in the XZ-plane as viewed along the section line 25-25' in FIG. 24. The regions 155-2 and 155-3 are show in FIG. 26 in a first layer 51"-1 at the locations where they cross the center line 25-25' in FIG. 24 in the following order 155-3', 155-2', 155-3, 155-2, 155-1, 155-2", 155-3", 155-2''' and 155-3'''. In FIG. 26, a second layer 51"-2 is a circular linear magnet under and the same size as the center 155-1 in layer 51"-1.

In FIG. 27, a schematic representation of the magnetic field in the XZ-plane of the magnet 51"-A of FIG. 26 is shown in an expanded view offset from the support 15. The magnetic field in the XZ-plane of FIG. 27 is a section view taken along the section line 4-4' in FIG. 1 when the magnets 51"-A and 51"-B and the pad 20 are used in the support 10. In FIG. 27, the support 10 and pad 20 are not pressed against a user and hence the pad 20 is not depressed into the trough 15-1 and the field pattern is as shown in FIG. 25. When the pad 20 is depressed into the trough 15-1, the field pattern is changed as shown in the circle in FIG. 27. Although the field is somewhat altered by depression into the trough 15-1 as shown in the circle in FIG. 27, the efficacy of the magnetic field is not materially altered and tends to flood the lumbar region.

Figure 28:
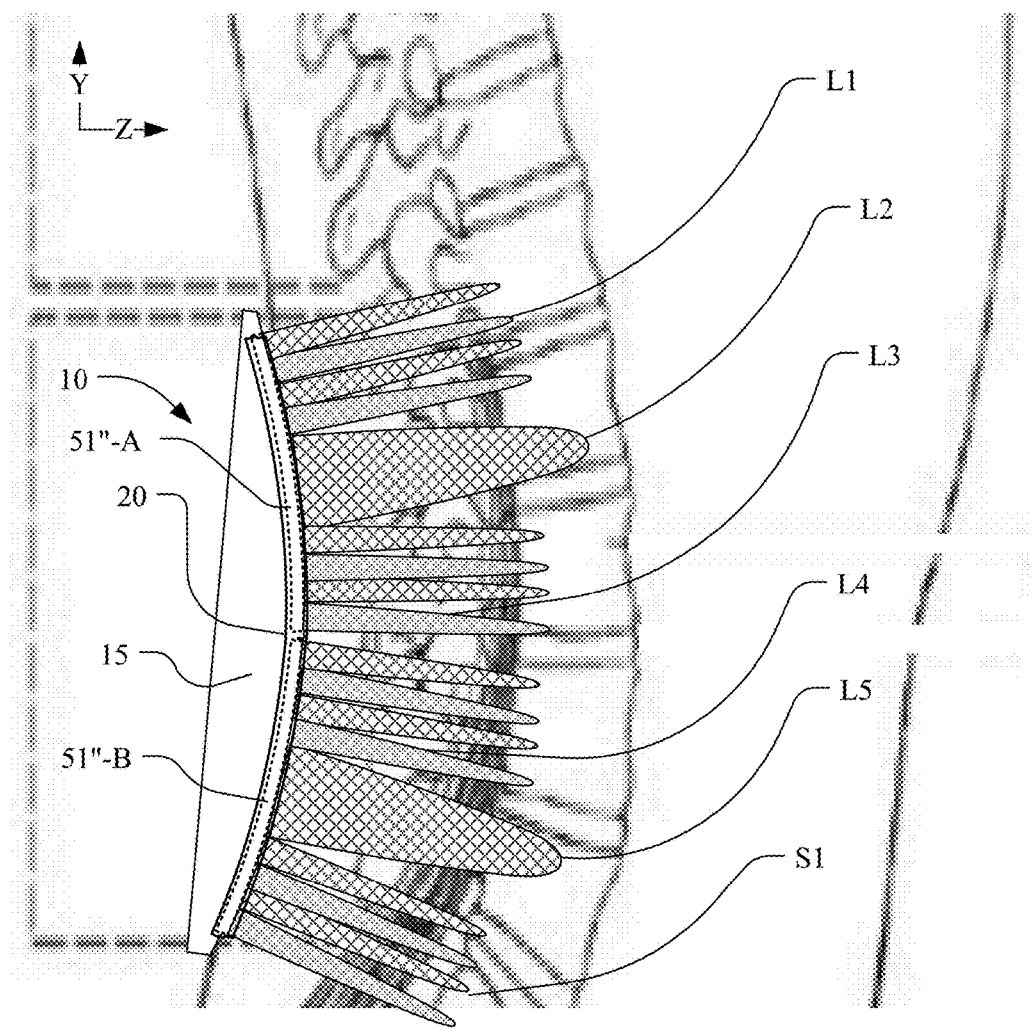
FIG. 28 depicts a schematic representation of the support positioned as shown in FIG. 7 with a magnetic field, shown in a plane in the YZ-plane direction, of the magnets of FIG. 24.

In FIG. 28, a schematic representation of the a template surface 15 as shown in FIG. 3 is positioned as shown in FIG. 7 with a magnetic field section along section line 3-3' in FIG. 2, shown in the YZ-plane, when the magnets 51"-A and 51"-B and the pad 20 of FIG. 24 are used in FIG. 2. The magnetic field from the magnets 51"-A and 51"-B extends into the lumbar region and the sacral region where the curvature of the pad 20 and the magnets 51"-A and 51"-B matches the curvature of the spine vertebrae. The lumbar region includes the five vertebrae L1, L2, L3, L4 and L5 between the rib cage and the pelvis and extends to S1 in the sacral region. These vertebrae are the largest segments of the vertebral column and are characterized by the absence of the foramen transversarium and facets on the sides of the body. The strength of the field is as described in connection with FIG. 12. The sacral region includes S1, S2, S3, S4 and S5 where S1 is next after L5.

It is apparent from the above description that an orthopedic support 10 for wearing about the lumbar region of a user is described. The support 10 has a smoothly contoured body, including a magnetic pad 20, with a template surface 15 bounded by an upper margin 18 and a lower margin 19. The support 10 and the magnetic pad 20 include a central trough portion 15-1 extending between the upper margin 18 and the lower margin 19 for accommodating the spinal processes of a wearer when the magnetic pad 20 is pressed by support 10 against the lumbar region. The support 10 and the magnetic pad 20 include two raised plateau regions 15-2 and 15-3 flanking the central trough portion 15-1 for contacting the erector spinae muscles of the wearer to provide support therefor. The central trough 15-1 and the plateau regions 15-2 and 15-3 form a smoothly curving surface 15 approximating the lordotic curve of a wearer to assist maintaining spinal posture. The orthopedic support 10 includes a magnetic pad 20 conforming to the contoured template surface 15, when engaged on a user, and extending between the margins 18 and 19 and extending over the central trough 15-1 and the two raised plateau regions 15-2 and 15-3 to provide a therapeutic magnetic field to the lumbar region. In the embodiment described, the magnetic pad is formed of one or more concentric circle magnets such as concentric circle magnets 51 and 52 containing concentric circle partitions 55 and 56.

While the invention has been described in connection with the embodiments of FIG. 8, FIG. 17, and FIG. 24 and variations thereof, further and other embodiments are also included. FIG. 8 includes a center ring and five concentric rings and FIG. 17 includes a center ring and two concentric rings. However, any number of concentric rings can be employed. Additionally, although concentric circles are described, concentric ovals, helixes or other shapes providing alternating north (N) and south (S) fields along major axes can be employed. In FIG. 13 and in FIG. 20, linear magnets 51-2 and 51'-2 are added below the center ring. In alternate embodiments, linear magnets can extend under one or more of the concentric rings to increase the magnetic amplitude of the field created by such rings. In FIG. 24, linear magnets 51-2 and 51'-2 can added below the center 155-1 for magnets 51"-A and 51"-B. Additionally, in FIG. 24, additional linear magnets can be provided under the helixes 155-2 and 155-3 in order to increase the strength of the magnetic fields.

The orthopedic support 10 is capable of providing a magnetic field including at least one composite static magnetic field by combining at least one of a bipolar static magnetic field and an axial static magnetic field and optimizing the spatial distribution and amplitude of the composite static magnetic field for a target pathway. The orthopedic support 10 is capable of providing a magnetic field satisfying a mathematical model including a Larmor precession model. The orthopedic support 10 in some embodiments couples one composite static magnetic field to said target pathway structure using a composite static magnetic device.

While the invention has been particularly shown and described with reference to preferred embodiments thereof it will be understood by those skilled in the art that various changes in form and details may be made therein without departing from the scope of the invention.

The invention claimed is:
1. An orthopedic support for securing about a lumbar region of a wearer comprising,
 a smoothly contoured body having a firm template surface bounded by an upper margin and a lower margin including,
  a central trough extending between the upper and lower margins for accommodating the spinal processes of the wearer when the template surface is pressed against the lumbar region,
  two raised plateau regions having tops flanking said central trough for contacting the erector spinae muscles of the wearer to provide support therefor,
  the central trough and the plateau regions forming a smoothly curving surface approximating the lordotic curve of the wearer to assist maintaining spinal posture,
 a magnetic pad attached to the contoured template surface and extending between the margins and extending over the central trough between the two raised plateau regions to provide a therapeutic magnetic field to the lumbar region and wherein the magnetic pad is formed of a flexible binding material that is attached to the tops of the plateau regions in a first position when the template surface is not pressed against the lumbar region and is depressed into the central trough in a second position when the template surface is pressed against the lumbar region to assist in maintaining spinal posture.

2. The support of claim 1 wherein the magnetic pad is formed of a concentric circle magnet containing concentric circle partitions.

3. The support of claim 2 wherein the magnetic pad is formed of concentric circle first and second magnets where the first and second magnets are juxtaposed and where the first and second magnets are each centered on a line between the upper and lower margins.

4. The support of claim 3 wherein the first and second magnets each have multiple sections alternating North (N) and South (S) polarities.

5. The support of claim 4 wherein the first and second magnets each have a NSNSN configuration or a SNSNS configuration.

6. The support of claim 4 wherein the first and second magnets each have a SNSNSNSNSNS configuration or a NSNSNSNSNSN configuration.

7. The support of claim 2 wherein the concentric circle magnet contains a first layer formed of a center circle having a circle surface and a plurality of concentric circle partitions around the center circle, wherein the center circle is centered over the central trough, and wherein a second layer is formed of a linear magnet where the linear magnet is juxtaposed the center circle and where the polarity of the center circle and the linear magnet are the same.

8. The support of claim 7 wherein the magnitude of the magnetic field at the surface of the center circle of the concentric circle magnet is approximately 600 gauss.

9. The support of claim 1 wherein the lumbar region and the lordotic curve of the wearer form a lumbar angle and the template surface is configured to form a template angle whereby the template surface conforms the lumbar angle to the template angle when the template surface is pressed against the lumbar region to assist in maintaining spinal posture.

10. The support of claim 9 wherein the template angle is approximately 7 degrees.

11. The support of claim 1 wherein the lumbar region has a curvature for five spine vertebrae L1, L2, L3, L4 and L5 and wherein the magnetic pad forms a magnetic field that is configured to flood the lumbar region of the wearer including the five vertebrae L1, L2, L3, L4 and L5 and surrounding tissue.

12. An orthopedic support for securing about the lumbar region of a wearer comprising,
 a smoothly contoured body having a firm template surface bounded by an upper margin and a lower margin where the template surface is at a template angle configured to approximate a lumbar angle of the lumbar region of a wearer's torso, the body including, a central trough extending between the upper and lower margins for accommodating the spinal processes of the wearer when the template surface is pressed against the lumbar region, two raised plateau regions having tops flanking said central trough for contacting the erector spinae muscles of the wearer to provide support therefor, the central trough and the plateau regions forming a smoothly curving surface approximating the lordotic curve of the wearer to assist in maintaining spinal posture, a magnetic pad attached to the contoured template surface and extending between the margins and extending over the central trough between the two raised plateau regions to provide a therapeutic magnetic field to the lumbar region wherein, the magnetic pad is formed of concentric circle first and second magnets where the first and second magnets are juxtaposed and where the first and second magnets are each centered on a line centered over the central trough between the upper and lower margins, the first and second magnets each have multiple conic sections with alternating North (N) and South (S) polarities, the first and second magnets each contain a first layer formed of a center circle and a plurality of concentric circle partitions around the center circle and a second layer formed of a linear magnet juxtaposed the center circle where the polarity of the center circle and the linear magnet are the same, the magnetic pad is formed of a flexible binding material that is attached to the tops of the plateau regions in a first position when the template surface is not pressed against the lumbar region and is depressed into the central trough in a second position when the template surface is pressed against the lumbar region to assist in maintaining spinal posture.

13. The support of claim 12 wherein the first and second magnets each have a NSNSN configuration or a SNSNS configuration.

14. The support of claim 12 wherein the template angle is approximately 7 degrees.

15. The support of claim 12 wherein the magnetic pad forms a magnetic field for flooding the lumbar region of the wearer including five vertebrae L1, L2, L3, L4 and L5 and extending to S1 in the sacral region.

16. An orthopedic support for securing about a lumbar region of a wearer where the lumbar region includes spine vertebrae having a lordotic curve comprising, a smoothly contoured body having a firm template surface bounded by an upper margin and a lower margin where the template surface is at a template angle where the template surface is configured to press against the lumbar region of a wearer's torso, the body including, a central trough extending between the upper and lower margins for accommodating the spinal processes of the wearer when the template surface is pressed against the lumbar region, two raised plateau regions having tops flanking said central trough for contacting the erector spinae muscles of the wearer to provide support therefor, the central trough and the plateau regions forming a smoothly curving surface approximating the lordotic curve of the wearer to assist in maintaining spinal posture, a magnetic pad attached to the contoured template surface and extending between the margins and extending over the central trough between the two raised plateau regions to provide a therapeutic magnetic field to the lumbar region wherein, the magnetic pad is formed of concentric circle first and second magnets where the first and second magnets are juxtaposed and where the first and second magnets are each centered on a line between the upper and lower margins centered on the central trough, the first and second magnets each have multiple conic sections with alternating North (N) and South (S) polarities, the first and second magnets each contain a first layer formed of a center circle and two concentric circle partitions around the center circle and a second layer formed of a linear magnet juxtaposed the center circle where the polarity of the center circle and the linear magnet are the same, the magnetic pad is formed of a flexible binding material that is attached to the tops of the plateau regions in a first position when the template surface is not pressed against the lumbar region and is depressed into the central trough in a second position when the template surface is pressed against the lumbar region to assist in maintaining spinal posture.

17. The support of claim 16 wherein the magnetic pad forms a magnetic field for flooding the lumbar region of the wearer including five vertebrae L1, L2, L3, L4 and L5 and extending to S1 in the sacral region.

18. The support of claim 16 wherein the first and second magnets each have a NSNSN configuration or a SNSNS configuration.

* * * * *